(12) United States Patent
Horie

(10) Patent No.: US 6,186,989 B1
(45) Date of Patent: Feb. 13, 2001

(54) COVERING BAG FOR AN ARTIFICIAL ANUS OUTFIT AND A WEARING DEVICE FOR THE ARTIFICIAL ANUS OUTFIT

(75) Inventor: Hisao Horie, Sakurai (JP)

(73) Assignee: Horiekikaku Co., Ltd., Nara (JP)

( * ) Notice: Under 35 U.S.C. 154(b), the term of this patent shall be extended for 0 days.

(21) Appl. No.: 09/153,648

(22) Filed: Sep. 15, 1998

(30) Foreign Application Priority Data

Sep. 24, 1997 (JP) .................................................. 9-276381
Dec. 1, 1997 (JP) .................................................. 9-347081

(51) Int. Cl.[7] .................................................. A61F 5/44
(52) U.S. Cl. .................................................. 604/345
(58) Field of Search .................................. 604/332, 337–9, 604/345, 343, 340, 350

(56) References Cited

U.S. PATENT DOCUMENTS

| 2,064,586 | * | 12/1936 | Boser | 604/345 |
| 5,026,362 | * | 6/1991 | Willet | 604/345 |
| 5,248,308 | * | 9/1993 | von Emster | 604/337 |
| 5,607,412 | * | 3/1997 | Brown | 604/332 |
| 5,653,701 | * | 8/1997 | Millman | 604/345 |

* cited by examiner

Primary Examiner—John G. Weiss
Assistant Examiner—Carie Mager
(74) Attorney, Agent, or Firm—Koda & Androlia

(57) ABSTRACT

The covering bag of the present invention comprises a front sheet, a right back sheet disposed from the upper right to the lower left and a left back sheet disposed in the opposite direction from the upper left to the lower right, both the back sheets being disposed to partially cover the back side of said front sheet, in order to form a bag, whereby the skin contact plate of an artificial anus outfit can be exposed outside from a nearly triangular opening formed at a portion above the intersection of the oblique fringes of the back sheets. The covering bag is provided with fasteners at the outer periphery of the opening thereof. A belt to be used with the covering bag is also provided with fasteners at the outer periphery of a through hole thereof for supporting the artificial anus outfit, the fasteners being disposed in correspondence with the above-mentioned fasteners provided on the covering bag. The covering bag can be supported at least in the longitudinal direction of the belt and in a direction perpendicular to the longitudinal direction of the belt as desired in accordance with the combination of the fasteners to be engaged with each other.

2 Claims, 6 Drawing Sheets

COVERING BAG FOR AN ARTIFICIAL ANUS OUTFIT AND A WEARING DEVICE FOR THE ARTIFICIAL ANUS OUTFIT

TITLE OF THE INVENTION

A covering bag for an artificial anus outfit and a wearing device for the artificial anus outfit

BACKGROUND OF THE INVENTION

1. Field of the Invention

The present invention relates to a covering bag for an artificial anus outfit, and also relates to a wearing device for the artificial anus outfit, comprising the covering bag and a support belt.

2. Description of the Prior Art

An artificial anus outfit is used to store excrement discharged from an artificial anus in a bag-like container worn by a user, and the bag-like container is often covered with a covering bag to hide contents. However, it is troublesome to cover the bag-like container with the covering bag. In addition, when the user lies down with the bag-like container kept worn, the bag-like container may be pressed by the body of the user, and the contents of the container are apt to leak. FIGS. 6 to 9 are views showing the structure of a conventional artificial anus outfit which may cause the above-mentioned problem.

A so-called one-piece pouch is shown in FIGS. 6 and 7. The numeral 1 designates a bag-like container having a flat structure and made of plastics or the like. The numeral 2 designates an upper opening to which a skin contact plate 3 is installed. A lower opening 4 is closed with a removable clamp 5. The skin contact plate 3 is shaped like a ring having a central hole 3a and a flange 3b, and made of soft flexible plastics or the like. A skin protection agent layer is formed on the outer surface of the flange 3b, and the layer is covered with a removable cover sheet 6 when not in use. When this artificial anus outfit is used, the cover sheet 6 of the flange 3b is peeled off, the skin contact plate 3 is made contact with the skin around the artificial anus, the discharge portion (not shown) of the artificial anus is inserted from the central hole 3a to the upper opening 2 so as to be projected in the interior of the bag-like container 1, and the outfit is pressed appropriately by cloths and the like.

A so-called two-piece pouch is shown in FIG. 8. The skin contact plate 3 shown in FIG. 9 as an example is removably installed to the bag-like container 1. A ring-shaped member 2a made of soft plastics or the like is provided at the upper opening 2 of the bag-like container 1. A ring-shaped groove 2b is formed on the surface of the ring-shaped member 2a. A plurality of projections 2c each having a hole to which a string or the like is tied are provided at the peripheral fringe of the ring-shaped member 2a. Corresponding to the ring-shaped groove 2b of the ring-shaped member 2a, a ring-shaped projection 3c is formed on the skin contact plate 3 made of soft plastics or the like. The skin contact plate 3 can be secured to the main body of the container 1 by fitting the ring-shaped projection 3c in the ring-shaped groove 2b, and can be removed by reversing the above operation. Portions similar to those shown in FIGS. 6 and 7 are designated by the same reference numerals. Just as in the case of the above-mentioned one-piece pouch, a skin protection agent layer is formed on the outer surface of the flange 3b, and is covered with a removable cover sheet when not in use. When this two-piece type artificial anus outfit is used, the skin contact plate 3 is secured to the bag-like container 1, the cover sheet of the flange 3b is peeled off, and the skin protection agent layer is made direct contact with the skin around the artificial anus. In addition, the discharge portion of the artificial anus is inserted from the central hole 3a to the upper opening 2 so as to be projected in the interior of the main body of the container 1, and the artificial anus outfit is supported at the waist or shoulder via strings or the like tied to the projections 2c.

A belt shown in FIG. 10 can also be used to support the artificial anus outfit. More specifically, a through hole 12 is provided in a wide belt 11 made of soft cloth or the like, the bag-like container 1 of the artificial anus outfit is inserted through the through hole 12 from the back side to the front side of the belt 11. The belt 11 thus supports the artificial anus outfit so that the bag-like container 1 is positioned on the front side of the belt 11 and the skin contact plate 3 is positioned on the back side of the belt 11. Furthermore, the bag-like container 1 is set in a direction perpendicular to the longitudinal direction of the belt 11, the discharge portion of the artificial anus is inserted in the upper opening 2, the skin protection agent layer of the skin contact plate 3 is made contact with the skin, the belt 11 is wound and worn around the waist by engaging the clamps 13, 14 provided at both ends of the belt 11 with each other. If the skin contact plate 3 of the one-piece type or the ring-shaped member 2a of the two-piece type is soft and easily deformable, the plate 3 or the ring-shaped member 2a may be inserted through the through hole 12 of the belt 11 from the front side to the back side. In the case of the two-piece type, the skin contact plate 3 is fitted in the ring-shaped member 2a after the insertion in order to secure the plate 3 to the main body of the container 1.

In the descriptions of the present specification, the outside at the time of use is defined as the front side, and the skin side is defined as the back side.

In the usage conditions of both above-mentioned types, the bag-like container 1 of the artificial anus outfit is exposed outside, and discharged contents can be seen. To solve this problem, a covering bag 15 shown in FIG. 11 is generally used to store the bag-like container 1 so that the bag-like container 1 cannot be seen from outside. The covering bag 15 has an opening 16 at its upper portion on the back side, and a cover 17 being open downward is provided above the opening 16. Furthermore, an opening 18 being open along its entire width is provided at the lower portion of the covering bag 15 on the back side. The artificial anus outfit is stored or removed through the opening 18. The skin contact plate 3 of the stored artificial anus outfit is taken out of the upper opening 16 and exposed outside, and the covering bag 15 is in a condition of covering the bag-like container 1 of the artificial anus outfit.

However, the above-mentioned conventional covering bag 15 requires troublesome operations when the artificial anus outfit is stored through the lower opening 18 and the skin contact plate 3 is taken out of the upper opening 16, whereby operability is impaired.

In addition, when the artificial anus outfit is used, the bag-like container hangs down due to its own weight and furthermore due to the weight of its contents when it has contents. When the user lies down, a part of the bag-like container 1 is apt to be pressed under the body of the user. Eventually, the contents may be squeezed from the upper opening 2, thereby contaminating the skin, the belt 11, the covering bag 15 and the like, as well as the clothes.

SUMMARY OF THE INVENTION

In order to solve the above-mentioned problems, a first object of the present invention is to improve operability by facilitating the storage and removal operations of an artificial anus outfit into and from a covering bag. A second object of the present invention is to provide a wearing device for the artificial anus outfit, wherein the direction of the bag-like container of the artificial anus outfit can be changed so that the container cannot be pressed when a user lies down.

In order to attain the above-mentioned objects, the covering bag in accordance with the present invention is intended to store an artificial anus outfit having a skin contact plate at the upper portion of a bag-like container, and comprises a front sheet, a right back sheet disposed to partially cover the back side of the front sheet, the peripheral fringe thereof from the upper right to the lower left being joined to the peripheral fringe of the front sheet, and the oblique fringe thereof not joined to the front sheet but open and formed straight from the upper right to the lower left, and a left back sheet disposed to partially cover the back side of the front sheet, the peripheral fringe thereof from the upper left to the lower right being joined to the peripheral fringe of the front sheet, and the oblique fringe thereof not joined to the front sheet but open and formed straight from the upper left to the lower right, wherein a nearly triangular opening is formed at a portion above the X-shaped intersection of the oblique fringes of the back sheets so that the skin contact plate of the artificial anus outfit can be exposed outside from the opening while the artificial anus outfit is stored in the covering bag.

In addition, a wearing device for an artificial anus outfit in accordance with the present invention comprises a covering bag for an artificial anus outfit, and a belt for supporting the artificial anus outfit stored in the covering bag. The covering bag has, on the back side thereof, an opening for allowing a skin contact plate provided at the upper portion of the bag-like container of the artificial anus outfit stored therein to be exposed outside, and is provided with one or plural clamps at the outer periphery of the opening. The belt has a through hole for supporting the artificial anus outfit in a condition wherein the bag-like container of the artificial anus outfit is disposed on the front side and the skin contact plate is disposed on the back side. In addition, at the outer periphery of the through hole, one or plural clamps are provided in correspondence with the above-mentioned clamps on the covering bag. Furthermore, the clamps on the covering bag and the clamps on the belt are provided so that the covering bag can be supported at least in the longitudinal direction of the belt and in a direction perpendicular to the longitudinal direction of the belt.

The covering bag having the above-mentioned structure can be used as a covering bag to be used with the wearing device of the artificial anus outfit. Furthermore, the covering bag comprises a front sheet, and a back sheet disposed on the back side of the front sheet to cover at least the lower portion of the front sheet, the lower peripheral fringe from one fringe thereof to the other fringe being joined to the lower peripheral fringe of the front sheet, and the upper fringe thereof not joined to the front sheet but open. Because of this bag structure, the artificial anus outfit can be stored or removed through an opening formed at the upper fringe portion of the back sheet. In addition, it is possible to use a covering bag having a structure wherein one or plural clamps, disposed outside the skin contact plate of the artificial anus outfit in the case that the artificial anus outfit is stored in the covering bag, are provided on the back side of the front sheet.

The concrete structures of the covering bag and the wearing device for the artificial anus outfit will be made clear from the following descriptions regarding embodiments.

DETAILED DESCRIPTION OF THE PREFERRED EMBODIMENTS

Next, embodiments of the present invention will be described below.

Figure 1:
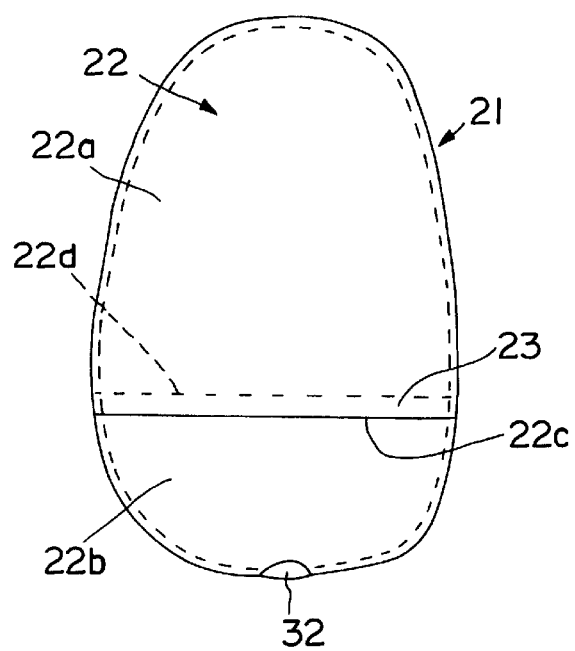
FIG. 1 is a front view showing a covering bag in accordance with an embodiment of the present invention.

Referring to FIG. 1, the numeral 21 designates a covering bag in accordance with the present invention. The covering bag is formed of opaque cloth or a soft plastic sheet. Although the entire shape of the covering bag shown in FIG. 1 as an example is oval, the outer shape of the covering bag is not limited to this shape, but can have another appropriate shape, such as a rectangular shape. The numeral 22 designates a front sheet comprising a large sheet 22a provided at the upper portion and a small sheet 22b provided at the lower portion. A straight-line opening 23 is provided at the overlap portion of the lower fringe 22c of the large sheet 22a and the upper fringe 22d of the small sheet 22b.

Figure 2:
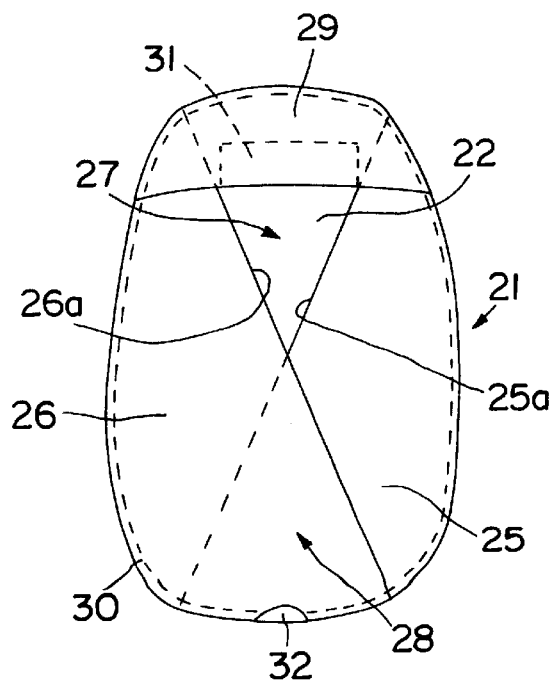
FIG. 2 is a rear view showing the covering bag.

At the back side of the front sheet 22, back sheets are provided to partially cover the front sheet 22. Referring to FIG. 2, the numeral 25 designates a right back sheet. Its peripheral fringe from the upper right to the lower left has the same shape as that of the peripheral fringe of the front sheet 22 and is joined to the peripheral fringe of the front sheet 22. An oblique fringe 25a not joined to the front sheet 22 is formed straight from the upper right to the lower left. On the other hand, the numeral 26 designates a left back sheet symmetrical with the right back sheet 25. Its peripheral fringe from the upper left to the lower right is joined to the peripheral fringe of the front sheet 22. An oblique fringe 26a not joined to the front sheet 22 is formed straight from the upper right to the lower left. Consequently, a nearly triangular opening 27 is formed at a portion above the X-shaped intersection of the oblique fringes 25a, 26a of the back sheets. Except for this opening 27, a bag 28 is formed by the back sheets 25, 26 and the front sheet 22. In addition, a cover 29 being open downward is provided at the upper portion. This cover 29 may be omitted, however.

Numeral 30 designates a seam for joining the back sheets 25, 26 and the cover 29 to the front sheet 22 by sewing. Instead of sewing, bonding or other joining means can also be used. Furthermore, when the entire shape of the covering bag is rectangular for example, the right and left portions of the front sheet 22 can be folded to form back sheets 25, 26, and only the lower fringes of the back sheets 25, 26 can be joined to the front sheet 22. In this way, the covering bag can have structures other than that shown in FIG. 2.

Since the covering bag 21 has the above-mentioned structure, the opening 27 can be made larger by widening the space between the oblique fringes 25a, 26a. Therefore, an artificial anus outfit can be stored into or removed from the bag 28 easily, and the skin contact plate 3 of the stored artificial anus outfit can be taken out of and exposed backward from the opening 27. In order to securely maintain this condition and to prevent the covering bag 21 from falling, the opening 27 is desired to be narrowed when the skin contact plate 3 is taken out of the opening 27. The numeral 31 shown in FIG. 2 designates surface fasteners provided for this purpose. One fastener is provided on the inner side of the cover 29, and the other fastener is provided on the back side of the front sheet 22. In other words, by securing the cover 29 to the front sheet 22 by using the surface fasteners 31, the opening 27 can be narrowed, and the area around the upper opening 2 on the front side of the skin contact plate 3 can be supported securely, thereby preventing the covering bag 21 from falling.

Furthermore, instead of the surface fasteners 31, a clamp, such as a button or a hook, may also be used. When the surface fastener is used, if both or one of the front sheet 22 and the cover 29 is made of a material capable of being engaged with the surface fastener, the surface fastener 31 can be provided only on the front sheet 22 or the cover 29 in accordance with the presence of the material.

Furthermore, in the embodiment shown in FIG. 1, the front sheet 22 is divided into the large sheet 22a and the small sheet 22b, and the opening 23 used as the second opening is provided therebetween. With this structure, it is also made possible to store and remove the artificial anus outfit through the opening 23. In addition, a part of the artificial anus outfit can be removed, washed or maintained as required while the belt is kept worn during the use of the artificial anus outfit attached to the belt. If these operations are not required, the opening 23 may be omitted.

Furthermore, the numeral 32 shown in FIG. 2 designates a hole. A urination pipe can be passed through this hole 32 for the sake of convenience.

Since the covering bag 21 shown in FIGS. 1 and 2 has the above-mentioned structure, the artificial anus outfit can be stored and removed easily, and the skin contact plate 3 can be exposed outside easily. However, the artificial anus outfit hangs down during use just as in the case of the conventional covering bag. Therefore, the possibility of pressing the bag-like container 1 when the user lies down still remains.

Figure 3:
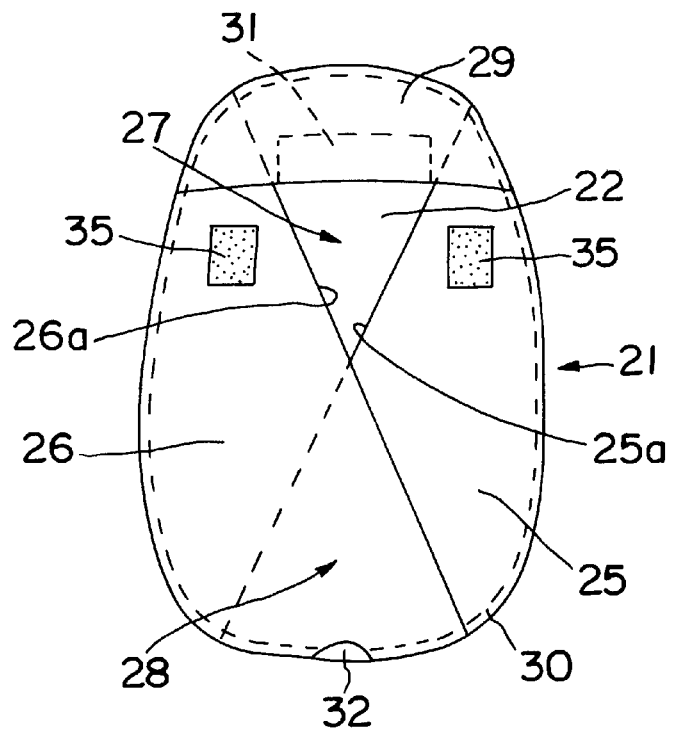
FIG. 3 is a rear view showing a covering bag in accordance with another embodiment.
Figure 4:
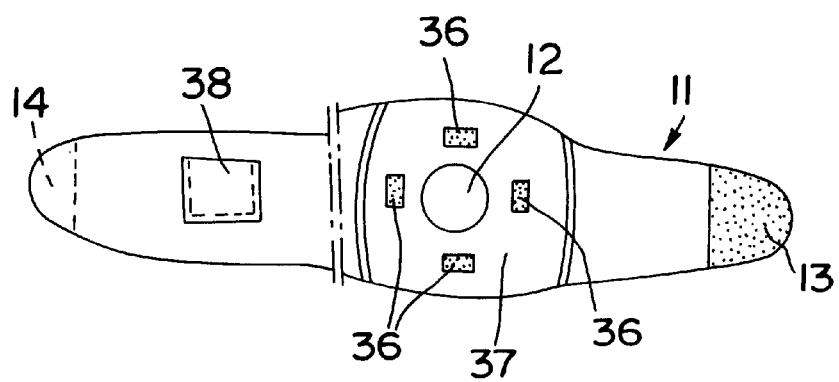
FIG. 4 is a front view showing the belt of a wearing device for an artificial anus outfit in accordance with an embodiment of the present invention.
Figure 10:
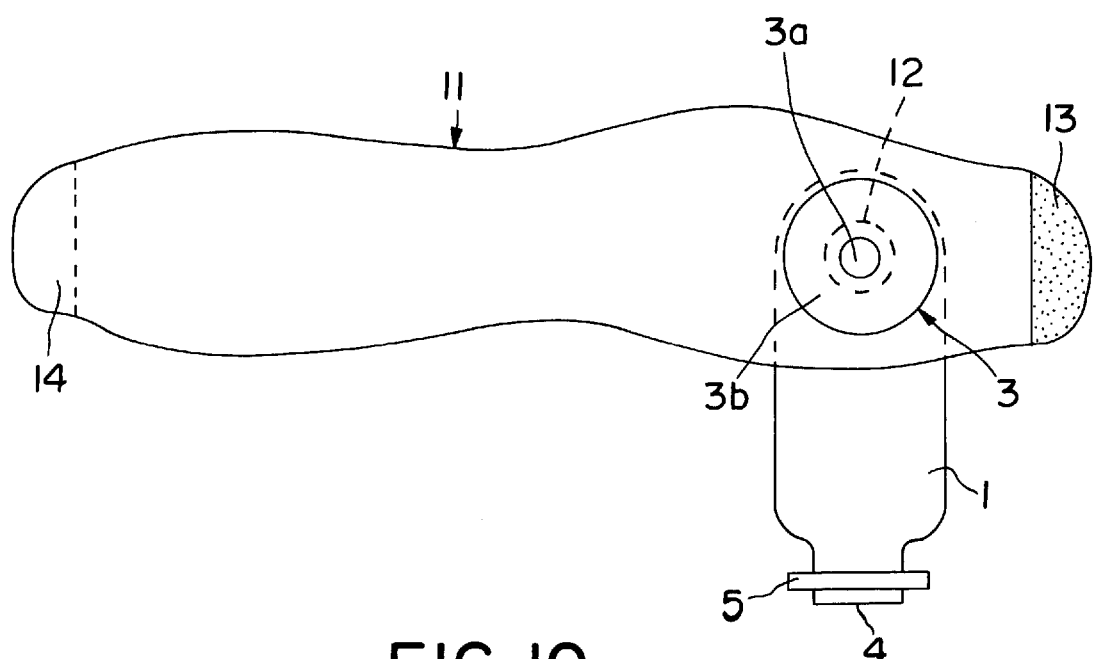
FIG. 10 is a rear view showing a condition wherein the artificial anus outfit is supported by a belt.

FIG. 3 shows a covering bag having been improved to solve the above-mentioned problem, and FIG. 4 shows a belt to be used together with this covering bag. As shown in FIG. 3, in this covering bag 21, the back sides of the back sheets 25, 26 are each provided with a surface fastener 35 at the right and left sides of the opening 27. Except for the fasteners, the structure of this covering bag 21 is basically the same as that of the above-mentioned covering bag. In addition, as shown in FIG. 4, surface fasteners 36 corresponding to the surface fasteners 35 on the covering bag 21 are provided at the outer periphery of a through hole 12 on the front side of a belt 11. In the embodiments shown in FIGS. 3 and 4, the surface fasteners 35 are provided at the right and left sides of the opening 27, and the surface fasteners 36 are provided at the right and left sides and the upper and lower sides of the through hole 12. In the case that the belt 11 is elastic, it is desirable that the area around the through hole 12 is covered with an auxiliary sheet 37 formed of less elastic cloth or a plastic sheet made of vinyl or the like, and that the surface fasteners 36 are installed on the auxiliary sheet 37. The numeral 38 designates a pocket capable of storing a spare artificial anus outfit and the like. Except for the above-mentioned points, the structure of the belt is basically the same as that shown in FIG. 10. Instead of the surface fasteners 35 and 36, buttons, hooks or the like can also be used.

When the artificial anus outfit is supported by the belt 11 by using the through hole 12, the covering bag 21 shown in FIG. 3 is used to cover the bag-like container 1, and the skin contact plate 3 taken out of the opening 27 is positioned on the back side. When the user stands, the surface fasteners 35, 35 of the covering bag 21 are engaged with the surface fasteners 36, 36 provided on the right and left sides of the through hole 12 in the belt 11. With this engagement, the covering bag 21 is disposed in a direction perpendicular to the longitudinal direction of the belt 11, and the artificial anus outfit stored in the covering bag 21 is also disposed in a direction perpendicular to the longitudinal direction of the belt 11. In addition, when the user lies down, the above-mentioned engagement is released once, and the surface fasteners 35, 35 of the covering bag 21 are engaged with the surface fasteners 36, 36 provided on the upper and lower sides of the through hole 12. With this engagement, the covering bag 21 is disposed in the longitudinal direction of the belt 11, and the artificial anus outfit stored in the covering bag 21 is also disposed in the longitudinal direction of the belt 11. Therefore, there is no possibility of pressing the bag-like container 1 unless the artificial anus is placed under the body due to careless turning over of the user, thereby preventing a problem of squeezing the contents of the baglike container 1.

When the artificial anus outfit is supported by the belt 11 and the belt 11 is worn around the body, it is desired that the artificial anus outfit is covered with a bridge-shaped cover or a pad having an appropriate thickness is disposed at each of both ends of the artificial anus outfit to prevent the artificial anus outfit from being directly pressed by the clothes.

The installation intervals and positions of the surface fasteners 35 and 36 should be determined so that the covering bag 21 can be disposed at least in the longitudinal direction of the belt 11 and in a direction perpendicular to the longitudinal direction. Furthermore, since the upper opening 2 of the artificial anus outfit is passed through the opening 27 of the covering bag 21 and the through hole 21 of the belt 11, the passing through portions and a single fastener 35 can control the direction of the covering bag 21. Furthermore, instead of the rectangular shape shown in FIGS. 3 and 4, the fasteners can have a circular shape or the like. Therefore, instead of the plural surface fasteners, a single fastener can be used to attain its purpose if its shape and location are modified appropriately.

Figure 11:
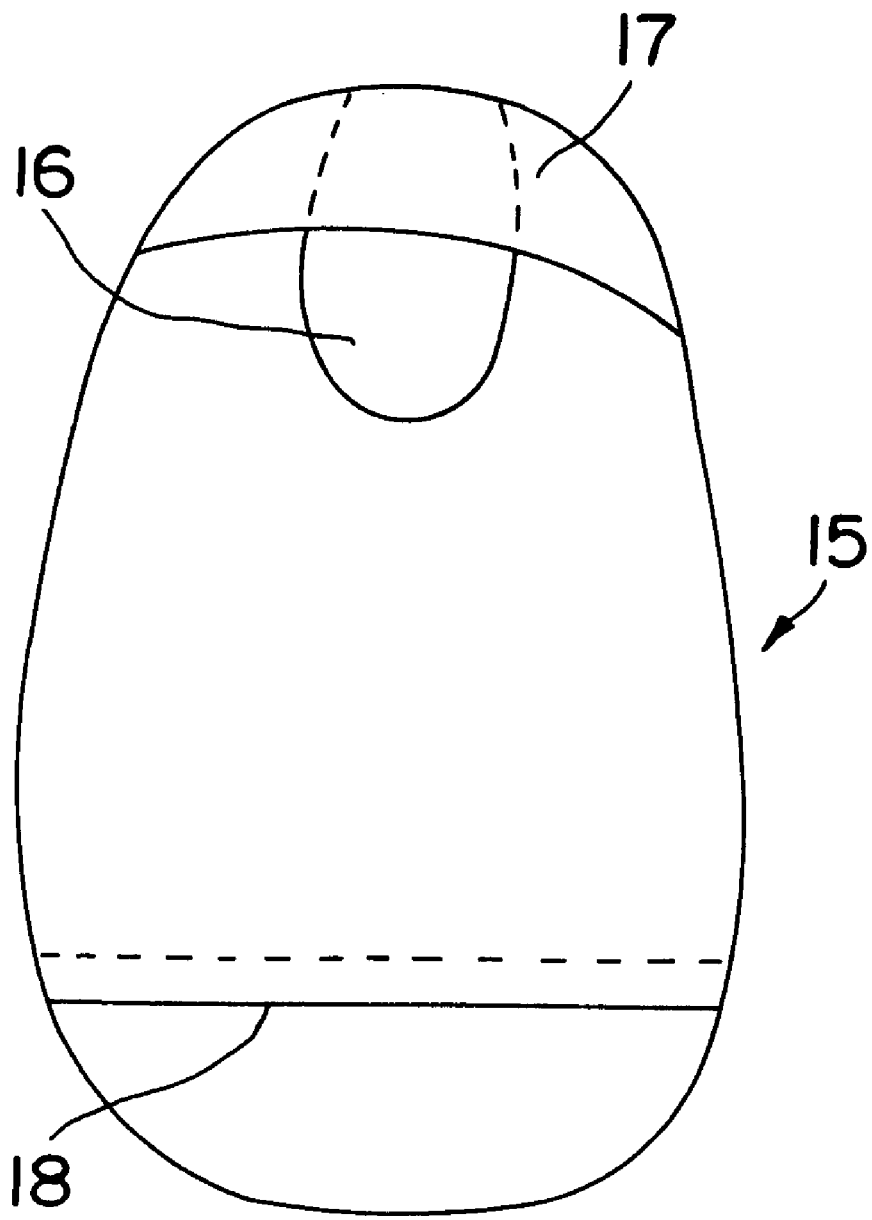
FIG. 11 is a rear view showing a conventional covering bag.

In regard to the supporting direction of the covering bag, the same purpose as that described above can be attained by installing the surface fasteners on the back side of the conventional covering bag 15 shown in FIG. 11 in a manner similar to that shown in FIG. 3 and by combining the covering bag 15 with the belt 11 shown in FIG. 4.

Figure 5:
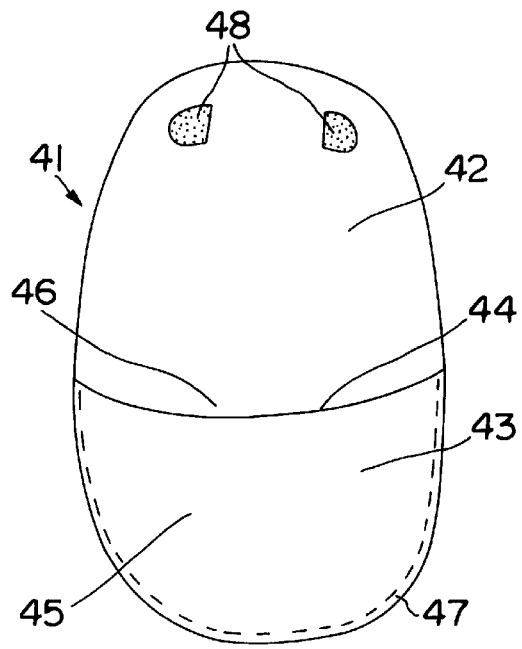
FIG. 5 is a rear view showing a covering bag in accordance with still another embodiment.
Figure 6:
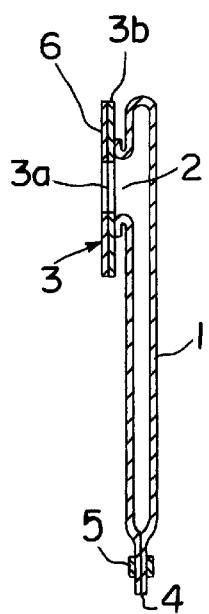
FIG. 6 is a sectional view showing a one-piece type artificial anus outfit.
Figure 7:
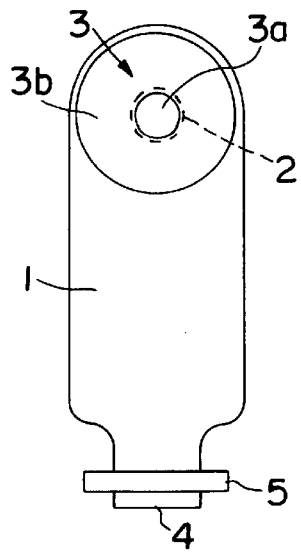
FIG. 7 is a rear view of the artificial anus outfit.
Figure 8:
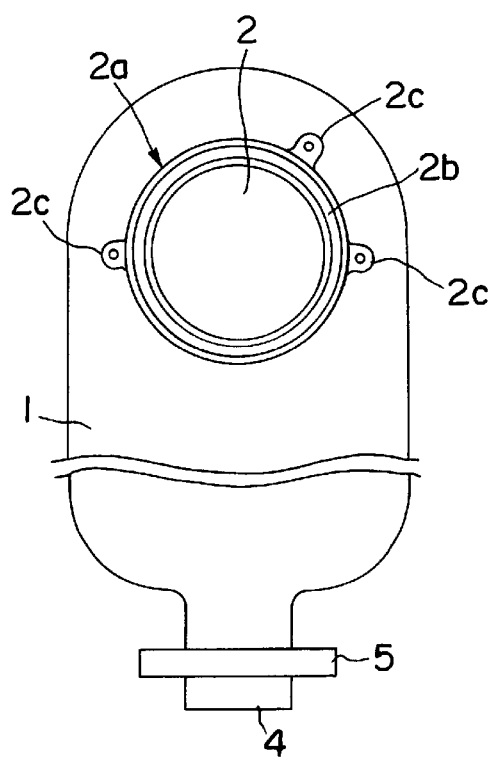
FIG. 8 is a rear view showing the bag-like container of a two-piece type artificial anus outfit.
Figure 9:
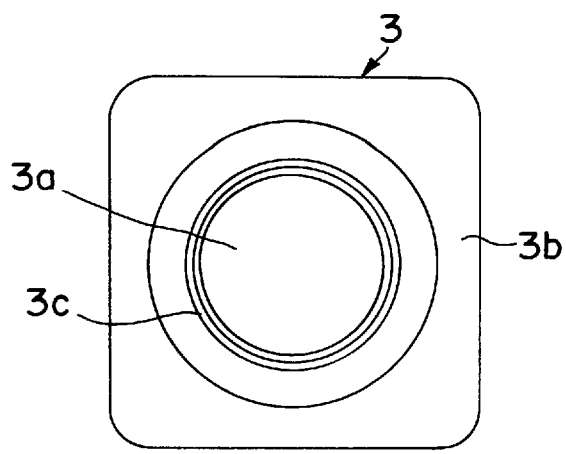
FIG. 9 is a front view showing the skin contact plate of the artificial anus outfit.

FIG. 5 shows a covering bag 41 in accordance with another embodiment. The numeral 42 designates a front sheet. A back sheet 43 formed to cover the lower portion of the front sheet 42 is provided on the back side of the front sheet 42. The lower peripheral fringe from one side to the other of the back sheet 43 is joined to the lower peripheral fringe of the front sheet 42, having the same shape as the lower peripheral fringe of the back sheet 43. In addition, the back sheet 43 has an upper fringe 44 which is not joined to the front sheet 42 but open. With this structure, a pocket-like bag 45 is formed, and an opening 46 is formed at the upper fringe 44. The upper fringe 44 may be straight or curved.

The numeral 47 designates a seam for joining the back sheet 43 to the front sheet 42 by sewing. Instead of sewing, bonding or other joining means can also be used. Furthermore, when the lower portion of the front sheet 42 has a rectangular shape for example, the lower portion can be folded to form the back sheet 43, and only the right and left fringes of the back sheet 43 can be joined to the front sheet 42. In this way, the covering bag can have structures other than that shown in FIG. 5.

At the back upper portion of the front sheet 42, a pair of surface fasteners 48 are provided in correspondence with the surface fasteners 36 on the belt 11. Just as in the above-mentioned case, when the artificial anus outfit is used, the artificial anus outfit is supported by the belt 11 by using the through hole 12, and the bag-like container 1 is stored in the covering bag 41. The above-mentioned surface fasteners 48 are provided at positions where the fasteners 48 do not interfere with the skin contact plate 3 while the artificial anus outfit is supported by the belt 11, preferably at positions near the outer periphery of the skin contact plate 3.

During use, the bag-like container 1 is stored in the covering bag 41, and the surface fasteners 48 on the covering bag 41 are engaged with the surface fasteners 36 on the belt 11. When the surface fasteners 48 are engaged with the right and left surface fasteners 36, 36 of the belt 11, the covering bag 41 is installed in a direction perpendicular to the longitudinal direction of the belt 11, and the artificial anus outfit stored in the covering bag 41 is also supported in a direction perpendicular to the longitudinal direction of the belt 11. Furthermore, when the surface fasteners 48, 48 on the covering bag 41 are engaged with the upper and lower surface fasteners 36, 36 of the belt 11, the covering bag 41 is installed in the longitudinal direction of the belt 11, and the artificial anus outfit stored in the covering bag 41 is also supported in the longitudinal direction of the belt 11. In this way, the installation direction of the artificial anus outfit can be determined as desired in accordance with the posture of the user. A problem of squeezing the contents of the container can thus be prevented unless the user, lying down, turns over carelessly.

The shape, number, installation positions, etc. of the surface fasteners 48 should be determined so that the covering bag 21 can be supported at least in the longitudinal direction of the belt 11 and a direction perpendicular thereto depending on the combination with the surface fasteners 36 of the belt 11. Instead of the surface fasteners 48 and 36, buttons, hooks or the like may also be used.

What is claimed is:

1. A wearing device for storing and supporting an artificial anus outfit comprising a covering bag for covering an artificial anus outfit and a belt for supporting said covering bag, wherein said covering bag has, on a back side thereof, an opening for allowing a skin contact plate provided at an upper portion of a bag-like container of said artificial anus outfit to be exposed outside of said covering bag, and is provided with at least one bag fastener at an outer periphery of said opening, said belt has a through hole for said artificial anus outfit when said bag-like container of said artificial anus outfit is disposed on a front side of said belt and said skin contact plate is disposed on the back side of said belt, at least one belt fastener is provided at an outer periphery of said through hole in said belt in correspondence with said bag fastener on said covering bag, and said bag fastener on said covering bag and said belt fastener on said belt are provided so that said covering bag can be supported at least in a longitudinal direction of said belt and in a direction perpendicular to said longitudinal direction of said belt and wherein said covering bag comprises a front panel and a pair of back panels and overlapping pockets formed from said pair of back panels which are attached to portions of a peripheral edge of said front panel, and the pair of back panels are also having overlapping oblique edges which are unattached to the front panel, forming on X-shape intersection of the edges and a V-shaped opening in an upper portion of the covering bag which allows for the widening of the opening when said bag like container of said artificial anus outfit is being inserted or removed from the covering bag.

2. A wearing device for an artificial anus outfit in accordance with claim 1, wherein said covering bag is provided with a second opening on said front sheet thereof so that said artificial anus outfit can also be stored or removed through said second opening.

\* \* \* \* \*